(12) United States Patent
Harper et al.

(10) Patent No.: US 7,293,645 B2
(45) Date of Patent: Nov. 13, 2007

(54) METHOD FOR MONITORING HAND HYGIENE COMPLIANCE

(76) Inventors: Judith Lee Harper, 16541 Redmond Way, Pmb 140, Redmond, WA (US) 98052; William Anthony Harper, 16541 Redmond Way, Pmb 140, Redmond, WA (US) 98052

( * ) Notice: Subject to any disclaimer, the term of this patent is extended or adjusted under 35 U.S.C. 154(b) by 1078 days.

(21) Appl. No.: 10/356,766

(22) Filed: Jan. 30, 2003

(65) Prior Publication Data

US 2004/0150527 A1    Aug. 5, 2004

(51) Int. Cl.
*A24F 15/00* (2006.01)
*B65D 85/10* (2006.01)
*B65D 85/12* (2006.01)

(52) U.S. Cl. .................. 206/205; 206/581; 206/210; 206/459.5; 222/107; 222/212

(58) Field of Classification Search ............ 340/573.1
See application file for complete search history.

(56) References Cited

U.S. PATENT DOCUMENTS

| | | | |
|---|---|---|---|
| 4,736,876 A * | 4/1988 | Kriss ..................... 224/148.1 |
| 5,202,666 A | 4/1993 | Knippscheer |
| 5,793,653 A | 8/1998 | Segal |
| 5,812,059 A | 9/1998 | Shaw |
| 5,945,910 A | 8/1999 | Gorra |
| 5,960,991 A * | 10/1999 | Ophardt ......................... 222/1 |
| 6,065,639 A * | 5/2000 | Maddox et al. ............... 222/36 |
| 6,236,317 B1 * | 5/2001 | Cohen et al. ............ 340/573.1 |
| 6,236,953 B1 | 5/2001 | Segal |
| 6,278,372 B1 | 8/2001 | Velasco |
| 6,375,038 B1 * | 4/2002 | Daansen et al. ............... 222/52 |
| 6,392,546 B1 * | 5/2002 | Smith ..................... 340/573.1 |
| 6,404,837 B1 * | 6/2002 | Thompson et al. ........... 377/13 |
| 6,426,701 B1 * | 7/2002 | Levy et al. .............. 340/573.1 |
| 6,882,278 B2 * | 4/2005 | Winings et al. .......... 340/573.1 |
| 6,945,426 B2 * | 9/2005 | Gentzkow et al. .......... 220/751 |
| 7,135,011 B2 * | 11/2006 | Powers et al. .............. 604/310 |
| 2006/0192031 A1 * | 8/2006 | Yeung ........................ 239/327 |

OTHER PUBLICATIONS

Earl, M. L.; Jackson, M. M. and Richman, L. S. (2001), Improved Rates of Compliance with Hand Antisepsis., Guidelines; *American Journal of Nursing*; Mar. 2001; 101 (3): 26-33.
Pittet, D. (2002), Promotion of Hand Hygiene: Magic, Hype, or Scientific Challenge?; *Infection Control and Hospital Epidemiology*; Mar. 2002; 23(3).
Boyce, J. M. (2000), Using Alcohol for Hand Antisepsis—Dispelling Old Myths; *Infection Control and Hospital Epidemiology*; Jul. 2000; 21(7).
Boyce, J. M. (2001) Antiseptic Technology: Access, Affordability, and Acceptance; Emerging Infectious Diseases; Mar.-Apr. 2001; 7(2): 231-233.
Dyer, D. L.; Shinder, A.; Shinder, F. (2000), Alcohol-free Instant Hand Sanitizer Reduces Elementary School Illness Absenteeism; Family Medicine; Oct. 2000; 32(9): 633-8.

* cited by examiner

*Primary Examiner*—Benjamin C. Lee
*Assistant Examiner*—Eric M. Blount

(57) ABSTRACT

While clean, disinfected hands are widely recognized as a principle means for controlling the spread of infections, disease, and similar health problems to both self and others, the prompt and repeated application of such materials as soap and water or waterless gels is necessary to maintain sanitary hands. So well recognized is this fact that many professional and governmental guidelines backed by regulations have been drawn to enforce compliance. This invention relates to compliance monitoring of hand sanitizing fluids and gels used to reduce the hand-borne transmission of pathogens. Disclosed is a simple, low-cost method of which a key aspect is the employment of a wristband dispenser with plural individual applications of hand sanitizing fluid in a convenient dispensing form. Inclusion of a use activated timing device provides a means of monitoring an individual's elapsed time since last use.

25 Claims, 2 Drawing Sheets

METHOD FOR MONITORING HAND HYGIENE COMPLIANCE

BACKGROUND OF THE INVENTION

This invention relates to compliance monitoring of hand sanitizing fluids and gels utilized to reduce the hand-borne transmission of pathogens. Disclosed is a simple, low-cost method of which a key aspect is the use of a wristband and similar worn or carried dispensers with plural individual applications of hand sanitizing fluid in a convenient dispensing format. One embodiment of the method uses a wrist-mounted dispenser that overcomes recognized and longstanding problems that contribute to inadequate hand sanitation, the single most important factor in causing nosocomial infections. To understand why professional and governmental guidelines backed by regulations have been drawn to enforce hand hygiene compliance, and how the instant invention facilitates an effective compliance monitoring method, it is necessary to appreciate the scope and nature of the health problems created by so simple a thing as unsanitary hands.

Each year more than 2 million hospital acquired infections occur in the United States, costing some $4.5 billion in additional charges. The Centers for Disease Control estimates more than one-third of healthcare associated infections can be prevented through better infection control programs of which hand cleaning is the centerpiece for reducing the spread of such infections. Hospitals are only one of many organizations burdened with hand-borne disease costs. A recent school study found that classrooms that made hand sanitizing fluid dispensers simply available for use showed a 20% reduction in student absenteeism due to illness as well as a 10% decrease in teacher absenteeism. And these are but two groups that lend themselves to study. Large population segments like commuters, food handlers, eaters, clerks, caregivers, and others share the same risks and could reasonable expect significant personal benefits from improved hand hygiene. The overall societal, economic and health impacts of hand-borne pathogens is enormous; it is the intent of the present invention to substantially curtail this debilitating circumstance by providing a low-cost, minimally invasive method of self and institutional compliance monitoring of hand hygiene.

Several recent articles provide an understanding of the current level of technology available and further describe the significant limiting problems the present art faces.

In March 2001 an *American Journal of Nursing* article ("*Improved Rate of Compliance with Hand Antisepsis . . .* ") stated that 80,000 hospital deaths occur each year as a result of nosocomial infections contracted during their stays. Further, that "it's common knowledge that the hands of heath care workers can carry disease-causing organisms from one patient to another and that hand antisepsis before and after each patent contact is crucial to the prevention and control of nosocomial infection." The reasons most often cited by hospital staff for failing to clean their hands adequately are inconvenience and no time. Given the hectic and demanding nature of their workload these are not excuses but simply statements of reality. That convenience and time are critical factors in maintaining hand sanitation is underscored by the finding in this study that placing hand sanitizing fluid dispensers "in the hallways outside patient rooms were nearly 30 times more likely to be used than dispensers mounted anywhere inside the rooms." Yet the most disturbing finding of this study was that full compliance with hand antisepsis guidelines was an unrealistic goal. That while hand sanitizing fluids took less time than washing and the placement of numerous dispensers bottles made matters somewhat more convenient, even with the heightened attention impact of the study itself (the Hawthorne effect), compliance did not achieve more than 60% at any time during the study. And it is well understood that over time, after the study is done and gone, a drift back to much lower compliance rates is inevitable; the dispenser bottle becomes just one more thing in the room, like soap at the sink, to be used when time and convenience allows.

In March 2002 an article in *Infection Control and Hospital Epidemiology* ("*Promotion of Hand Hygiene: Magic, Hype, or Scientific Challenge?* ") restates the conditions for promoting adequate hand hygiene. "Among enabling factors, engineering control must be considered for the successful promotion of hand hygiene. In particular, it involves making hand hygiene easy, convenient, and possible in a timely fashion." Another observation made is that the higher rates of compliance seen in studies can only be sustained when some form of cost-effective, non-intrusive monitoring is invented. "My personal opinion is that obtaining a sustained and never-ending Hawthorne effect associated with improved compliance with hand hygiene and decreased infection and cross-transmission rates should be the dream of every hospital epidemiologist. Let's find a cost-effective way to induce it." This need has remained unfulfilled until now and the instant invention.

In July 2000 another article in *Infection Control and Hospital Epidemiology* ("*Using Alcohol for Hand Antisepsis—Dispelling Old Myths*") the qualities and values of alcohol-based hand antiseptics are described. The author points out the cost benefits of hand sanitizing fluids in hospitals. " . . . administrators should consider that modest increase in acquisition costs for alcohol-based hand hygiene products are tiny in comparison to excess hospital costs associated with nosocomial infections. If increased use of an alcohol gel or rinse reduces the number of serious nosocomial infections by a few a year, the cost savings from prevented infections should more than offset incremental costs of using alcohol-based preparations." These offset costs are those the hospital would charge as operational costs and are not insignificant. Another New York City Hospitals study placed the average additional cost at $35,000 per stay for just one type of pathogen, *Staphylococcus aureus*. Not considered are the much more substantial costs of the damage awards issuing from pain and suffering lawsuits won by patient and their attorneys for the hospital's failure to follow best practice protocols and compliance guidelines.

In March 2001 an article in *Emerging Infectious Diseases* ("*Antiseptic Technology: Access, Affordability, and Acceptance*") further reinforces the findings that time and convenience are critical compliance factors. Detailed costs of implementing a hand hygiene program are also provided.

A final article in the October 2000 issue of *Family Medicine* ("*Alcohol-free Instant Hand Sanitizer Reduces Elementary School Illness Absenteeism*") reports a remarkable reduction in absenteeism when hand sanitizers were introduced in public school classrooms. Results showed students using hand sanitizing fluids "were found to have 41.9% fewer illness-related absence days, representing a 28.9% and a 49.7% drop in gastrointestinal- and respiratory-related illness, respectively . . . . Conclusion: Daily use of the instant hand sanitizer was associated with significantly lower rates of illness-related absenteeism." In this study the close monitoring and continual instruction of the test group teachers largely abrogated the issues of time and convenience. Nevertheless, it clearly indicates the significant impact consistent and rigorous hand sanitation can have in schools and the implications for parallel benefits at all levels of society are obvious. As the reports point out in describing the interlinking cost of disease "Even if one doesn't have school-age children, it is necessary to understand the importance and benefits of good hand hygiene, not only in clinical practice but also in the greater community. Vital tax dollars will be saved on expenses for remedial student services and employee work time by this simple and effective way to decrease illness-related absenteeism."

That improved hand hygiene can be achieved by using various hand sanitizing fluids is beyond question; the problems preventing this known technique for achieving a high degree of use (compliance) are equally understood as being time and convenience. The instant invention of a novel compliance monitoring method is perforce based on a new form of dispenser of hand sanitizing fluid that mitigates the problems of time and convenience. A compact wrist mounted at hand package dispensing unitized hand sanitizing fluids largely overcome these twin problems and its inherent design features facilitates compliance monitoring.

This device in its many embodiments is the subject of a pending U.S. patent application Ser. No. (10/340,478) by William Harper. At its elemental base that applied for invention can be simply described as attaching a container of hand sanitizing fluid to the user's wrist and subsequently dispersing that fluid for application to the hands. By placing the dispenser at this critical part of the anatomy several benefits are immediately apparent: it is always at hand for instant use; it is close at hand to the point of application; its very presents on the wrist reminds the user to use the fluid; it takes no time to retrieve and return to pocket; and it requires no walking to and from a distant dispenser. These numerous at hand advantages have given that invention its name, the AtHand .TM. system. Compliance monitoring of the AtHand .TM. system utilizes a method that often relies upon several distinct advantages made possible by that system's unique characteristics To better understand how distinct theses advantages are it is beneficial to review the prior art of hand hygiene compliance monitoring as described in the United States patent literature. There have been numerous devices and methods developed for monitoring hand hygiene compliance, most in the last ten years. Eight patents that are representative and relevant in some manner defining the current art are as follows:

Knippscheer U.S. Pat. No. 5,202,666 disclosed a system where an employee wears a nametag that is sensed when the employee enters a washroom and again is sensed when leaving the washroom. A third sensing is created if an employee washes their hands. If the employee is sensed leaving the washroom without a hand-washing signal a command is issued to wash, their badge blinks, a computer record is made or a combination of such actions occurs.

Shaw U.S. Pat. No. 5,812,059 disclosed a reverse variation of Knippscheer '666 where the sensing zone is moved from the washroom to a designated clean area. When an employee wearing a transmitting badge enters or leaves and reenters a clean zone they are required to use a washstand in the clean area in a timely fashion or be tagged for non-compliance.

Segal U.S. Pat. No. 5,793,653 disclosed a hand sink equipped with and its water controlled by an ID input unit that records a time stamp and duration of use by the user. By networking many sinks a compliance profile on an individual is created for management review and action.

Gorra U.S. Pat. No. 5,945,910 disclosed a system where the compliance monitoring is placed in the washstation's dispenser of cleaning agents. The employee inputs their identification code and the dispenser's data module adds a time/date stamp creating an electronic record for later administrator collection, review, and action.

Segal U.S. Pat. No. 6,236,953 disclosed a washstation control system that operates on validating predetermined operating parameters of a given user. A communicating monitoring device capable of detecting and controlling water, cleaner dispenser use, and blower functions enforces compliance by data records and audio non-compliance warnings.

Velasco U.S. Pat. No. 6,278,372 disclosed an electronic badge that is capable of emitting a light which darkens, blinks or emits a sound if the badge is not reset after a predetermined time by the wearer when prompted to wash their hands.

Thompson U.S. Pat. No. 6,404,837 disclosed a hand soap dispensing unit that has a self-contained keypad/display module capable of recording a user's input identification code and storing data for later management extract and use.

Levy U.S. Pat. No. 6,426,701 disclosed an electronic badge activated by a beacon placed in a contaminated area. The wearer must wash their hands in an area covered by a deactivating beacon to deactivate the badge's contamination signal output.

The above described current practices, known expressions of these inventions in the marketplace, and all other known forms of compliance monitoring are all deficient is several respects. Significantly, none of the above references taken in part or as a whole present a convenient, timely, and effective way of facilitating hand hygiene other than those where a remote washstation is a key component in achieving the compliance goal. However organized, each invention includes a step of traveling to a predetermined physical place to perform an ablutionary act as a key action to be somehow sensed for compliance monitoring purposes. The instant invention is the first of a new class of compliance methods to move the sanitizing function to the person, worn or carried in some fashion by that person, and a physical record of those hand cleanings created at the moment of use whereby compliance monitoring is possible both instantly now and cumulatively later. As the literature has clearly and repeatedly stated, the biggest problem with achieving compliance regardless of the coercive tactics set to measure that compliance is to adequately address the issues of time and convenience first. To develop a technically successful sensing system monitoring compliance without also meeting the overarching need for sanitary hands at an operationally affordable price is simply missing the point. One report has estimated that nearly 20% of a staff nurse's time would be spent hand washing if a full regime of conventional washing compliance were followed; no healthcare facility could afford such a drain of staff time and money. Not only is the cost of the monitoring system largely wasted, but the very records it creates become a corporate liability in subsequent legal actions where failure to follow establish hygienic protocols becomes an issue. No system represented in the current art actually makes time and convenience the essential element of their compliance monitoring system. The AtHand .TM. system of hand sanitation with its built-in compliance monitoring features represents a new branch in the current state of the art.

SUMMARY OF THE INVENTION

The present invention recognizes and addresses the foregoing disadvantages and shortcomings of the prior art. Accordingly, it is a primary intent of the present invention to couple the time and convenience advantages of the AtHand .TM. system of worn or carried hand sanitizing fluid dispensers with a self-recording, low-cost, unintrusive monitoring method providing compliance data for management. This is made possible by recognition that all the essential input characteristics necessary for monitoring are already inherently in place in the AtHand .TM. system. First, the disposable dispenser is a personal item typically worn or carried on the body so any recorded activity is unalterable linked to one person, the wearer. No identification codes shared among friends, no dead batteries in smart badges that negates histories, and no malfunctioning or compromised transmitters to invalidate compliance data; just the dispenser bearing its physical record of the wearer's activities held in a format the wearer is personally responsible for creating. Second, the physical record of each dispensing act is self-documenting, no other record keeping imposes itself at this time of action. Third, the hand cleaning act does not require going to a physical washstation to perform; a nurse walking to the next patent's room can sanitize their hands walking down the hall without missing a step or taking a second longer. Fourth, compliance data in this method can be collected at shift end by as simple a technique as removing the disposable wristband dispenser, signing the back, and dropping it in a hopper for tabulation by management. Fifth, compliance monitoring can also be conducted by casually observing whether or not the dispensers are being worn and used; additionally, continuous spot checks for compliance whether by management or peers offers the very significant benefit of correction at the time of the infraction in contrast to days later in a personnel review. From the simple concept of the wrist mounted dispenser a number of expressions introduce a wide range of advantages and techniques as will be discussed by way of the examples provided in the detailed description of the preferred embodiments. Further objects of the present invention include:

It is an object of the present invention to provide a low-cost, low technology method of compliance monitoring useful to such operations as elementary schools, military installations, elder care facilities, police forces, and correctional institutions.

It is an object of the present invention to provide a no-cost, self-contained method where a parent can monitor their child's compliance in maintaining sanitary hands.

It is an object of the present invention to provide a no-cost, self-contained method where individuals can monitor their own compliance rate.

It is an object of the present invention to provide a method that avoids cross contamination common to other systems that rely on a common shared wash facility.

It is an object of the present invention to provide a compliance method wherein both the washing and compliance apparatus are carried or worn by the user.

It is an object of the present invention to provide a method that continually signals to clients that this establishment or institution takes the client's health seriously by practicing hand hygiene compliance.

It is an object of the present invention to provide a method that incorporates a lapse timing feature to discourage fraudulent record creation.

It is an object of the present invention to provide a method in which the data record can be readily converted by mechanical means to an electronic database as a resource for initiating informed management actions, to provide medical data for research, and forestall liability claims resulting from legal actions.

Other objects, features and aspects of the present invention are described in greater detail by the following exemplary embodiments. It is to be understood by one of ordinary skill in the art that these are exemplary embodiments only, and are not intended as limiting the broader aspect of the present invention, which broader aspects are embodied in the exemplary constructions.

BRIEF DESCRIPTION OF THE DRAWINGS

The invention will be better understood and objects other than those set forth above will become apparent when consideration is given to the following detailed description thereof. Such description makes reference to the annexed drawings wherein.

The same numbers reference the same elements in all the various figures.

DETAILED DESCRIPTION OF THE PREFERRED EMBODIMENTS

The present invention can best be understood by examples that illustrate how a dispenser of hand sanitizing fluid attached to a wrist or otherwise mounted or carried can contribute to a method of compliance monitoring.

Example 1

Monitoring with Blister Wells

Figure 1:
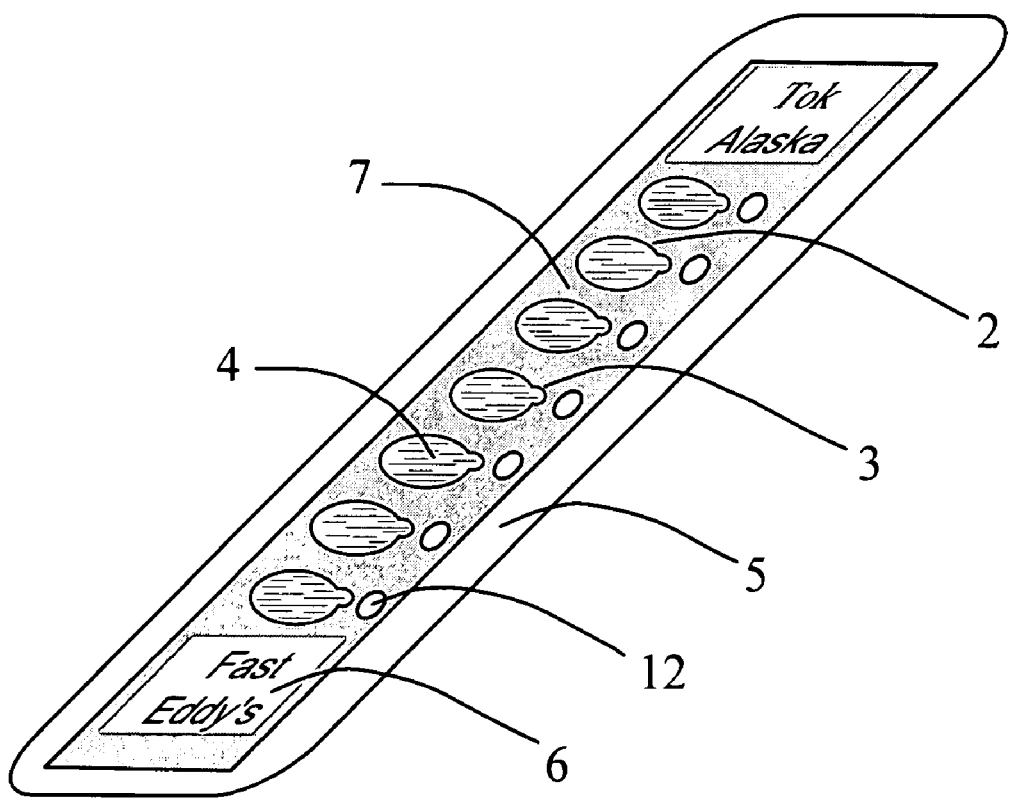
FIG. 1 is a frontal perspective view of a simple embodiment of a disposable dispenser package with multiple blister wells 2 formed in a top film, each containing a single application of hand sanitizing fluid 4, sealed to a stiff backine 5 in accordance with the principle of the present invention.
Figure 2:
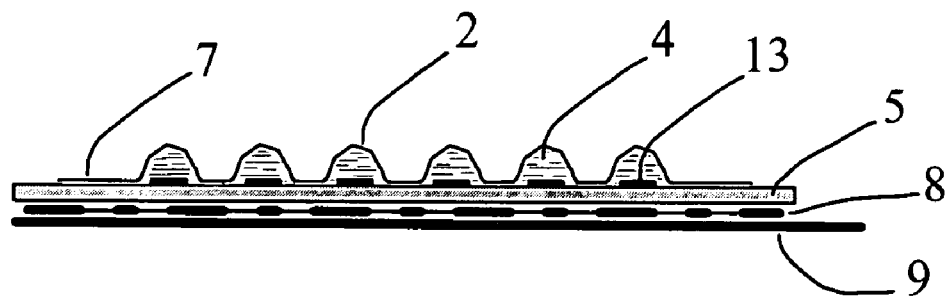
FIG. 2 is a cross-sectional side view showing the relationship of the plural wells 2, backing 5, sealing areas 7, affixing adhesive 8 and a removable cover 9 on the adhesive.

The dispenser is in the form of a common blister package card that contains a plurality of dosage wells containing hand sanitizing fluid. Each well is spaced at uniform distances from others and are typically 12 in number on the card's surface, although of course, various other alternative embodiments are easily imaginable and useful. Typically the number of wells might range between 2 and 30. Each of the wells has one basic requirement, the ability to hold and preserve the quality of the hand sanitizing fluid, typically a viscous liquid in the form of a gel such as found in several commercial offerings sold under the general designation of hand sanitizers. Each cell contains about 2 milliliters of hand sanitizing fluid, although the range of the dosage amount for an individual application can easily vary from about 0.5 ml to 5 ml depending on the product's formulation, sanitizing strength, and the coverage desired. The blister forming the well is flexible so that sufficient purposeful pressure on this flexible surface can release the hand sanitizing fluid within at a predetermined point such as rupturing at a specific point created in the design of the blister's surface. To permit adequate pressure buildup a relatively stiff and impervious backing placed in a sealing arrangement with the blister cover is required. This backing was applied in the manufacturing process after the blister wells were formed in the cover and filled with hand sanitizing fluid, sealed to the cover by heat or some like means, and thus forming one side of the container (gel filled cavity). Graphic representation of an embodiment of the multi-well, single dose disposable dispenser package is shown in FIG. 1 and FIG. 2. Seven blister wells 2 formed of flexible polymeric film (2-mil clear, coextruded polypropylene/polyvinyldichloride/polypropylene) enclose and contain a hand sanitizing fluid 4 (62% ethanol). The film with its filled wells 2 has a peripheral seal 7 with a relatively stiff non-rupturable backing 5 that facilitate handling by hands of varying size and strength, necessitates blister well side dispersement and effectively lids each of the wells 2. Creation of the seal can be achieved by a number of means well known in the art, herein the common technique involving heat and pressure is used to create the seal 7. Also illustrated is a release point 3 in the form of a weakened area of each well 2 wall created by design during the molding of the well 2 in the film to form a predetermined point for fluid 4 release. Immediately adjacent to the release point 3 is a timing dot 12 that when wetted by fluid 4 during dispersal can indicate the elapsed time since fluid dispersal from the associated blister well 2. Further illustrated in FIG. 1 is a mark 6 functioning as a simple cuing means for the package. FIG. 2 shows all the elements of FIG. 1 laid out as a cross-section which further depicts a package attachment means herein shown as an adhesive 8 with a removable cover 9. Also shown is an alternative placement to an externally timing dot 12 where an embed timing dot 13 is located within a blister well 2 and in contact with the fluid 4. The encapsulated hand sanitizing fluid is surrounded and sealed by impervious material that both retains and preserves the desirable properties of the fluid. The backing can do more than just form one side of a container; by extending its length beyond the blister cover wrapping straps are formed capable of encompassing a wrist. When the straps are further equipped with adhesives near the ends, the backing becomes a means for attaching the entire blister package to the wrist. Of course the adhesive forming a closure means could be any of other connecting types including buckles, buttons, clasps, fasteners, loops, magnets, pins, rivets, twists, ties, or Velcro hooks and loops. By attaching the blister package to the wrist by means of the backing straps, the flexible blisters are exposed to access. With sufficient pressure applied to a given flexible blister by the wearer in the form of a finger or thumb of the opposite hand a predetermined amount of hand sanitizing fluid is released from the well to be conveyed by the finger or thumb to the hands for application. The shape and design of the blister can greatly facilitate this fluid release while also contributing to the overall ergonomic aspect of the dispenser package. Some geometric forms anticipated include a circular ring, cone, cube, cylinder, disc, ellipsoid, frustum, hemisphere, oval, paraboloid, prism, pyramid, rectangular prism, spheroid and whole or partial combinations thereof. These form elements can be used to design where the rupture release point is to be by focusing the pressure buildup to a specific designated point and soften the burst out flow. Alternatively, the blister surface can be simply weakened by thinning a designated area of the blister wall during formation of the well. Another form of release is a group of release points characterized by a self-closing slit or puncture opening. The overall aspect of the disposable dispenser package attached to the wrist is of a device low in profile, lightweight, easily attached, non-interfering, readily accessible, and always at hand.

Use of the described dispenser means creates a discrete physical record of each dispersed application in the form of a ruptured or emptied well. By counting the physical record created by these wells using visual, tactile, or mechanical means a number is obtained that corresponds to the total acts of hand sanitation. Coupling this number with a the time period in which the person wore and used the dispenser it is possible to gauge the degree of hand sanitation the wearer engaged in during this period. By way of example, a group of twelve fast-food employees wear the AtHand .TM. bands during their various three hour shifts during a day. At the end of their shifts each employee signs the back of their disposable band and drops it in a hopper for the manager. The manager examines the bands and finds nine employees broke open six of ten wells on their bands in a three-hour shift, this meets the standard of compliance which experience has set at typically requiring two sanitizing acts per hour. Two employees used their bands more often than the standard, but one employee had only one use. The manager decides to observe and counsel this employee as necessary to maintain a high degree of uniform hand hygiene compliance for the establishment. This simple, low-cost form of compliance monitoring leading to an informed action is a key objective created by the instant invention.

In addition to the dispenser being worn on the wrist the apparatus may be worn anywhere on the body such as on the forearm, leg, shoulder, chest or elsewhere as may be suitable. The dispenser may also be hung about the neck by a lanyard by itself or associated with the ubiquitous identification badges now so prevalent. The dispenser may also be simply attached to clothing or carried in a pocket of the user. All manner of means by which the dispensers may be worn or carried as a personal item on or about the person are envisioned as long as the item remains principally a personal item.

A significant feature of this method is the creation of the physical record at the time of the dispersal for the act of rubbing hand sanitizing fluids. This record has other uses than just providing a counting means for emptied, ruptured or shape changed wells, it also offers a means of gauging when that dispersal occurred. When a well is ruptured or similarly emptied a certain residual amount of hand sanitizing fluid is left in the dispenser's area. By experimentation it has been found, depending on a number of factors including formulation, the fluid has a rate of evaporation that can be used to judge whether the dispersal act was recent or older in time. The duration period for an alcohol based formulation to evaporate from a wrist mounted dispenser from air exposure incurred in the act of dispersal to an air dried condition can ranges from 1 to 60 minutes; a typical 62% alcohol gel based formulation typically takes about 15 minutes to dry. This evaporation factor provides a useful tool in discouraging an employee from fraudulently discharging several wells at once when they see a supervisor coming for a spot compliance check. A further refinement that makes the evaporative factor more accurate and easier to read is the use of an absorbent masking layer of material located at the bottom of the well or as a timing dot at the exit point of the hand sanitizing fluid. This timing dot in its normal state, at the bottom of a fluid filled well, is transparent due to the fluid's optical qualities filling the open spaces and saturating the fibers of the masking material. The masking layer in this transparent state reveals a color or mark that is visible though the transparent blister, fluid and masking layer. But when the fluid is removed for a hand rubbing and the residual fluid evaporates out of the masking layer over a matter of minutes, the layer becomes opaque without the transmitting optical characteristics of the fluid and obscures the color or mark. The masking material need not be exotic, common cloth or paper as might be found in a paper towel will suffice and is in keeping with the low-cost disposable nature of the band envisioned. By placing the same technique of a timing dot outside the dispensing unit but in the path of the dispensed fluid so the dot is saturated by that action the pattern measuring the lapsed time from dispersal is reversed; the normal condition is the masking layer obscuring the color or mark but when saturated makes the color or mark visible but moving to obscuring as it dries. Common chemical technology is also available for timed chemical reactions with at least one of the fluid's formulation ingredients that can provide the element of elapsed time feature.

Counting the physical record to determine the number of applications can be done by either visual or tactile techniques. More complex but faster mechanical techniques can also be applied for the same end. Using a machine to count the physical record opens the possibility for many more elaborate processing activities including the rapid and direct creation of electronic database information that might include such features as bar code correlation of specific bands with an individual identification code of the wearer, matching the band with the wearers time of use, location of the wearer's activities, and a great range of similar data correlation useful to compliance monitoring.

Example 2

Monitoring a Single Reservoir

Figure 3:
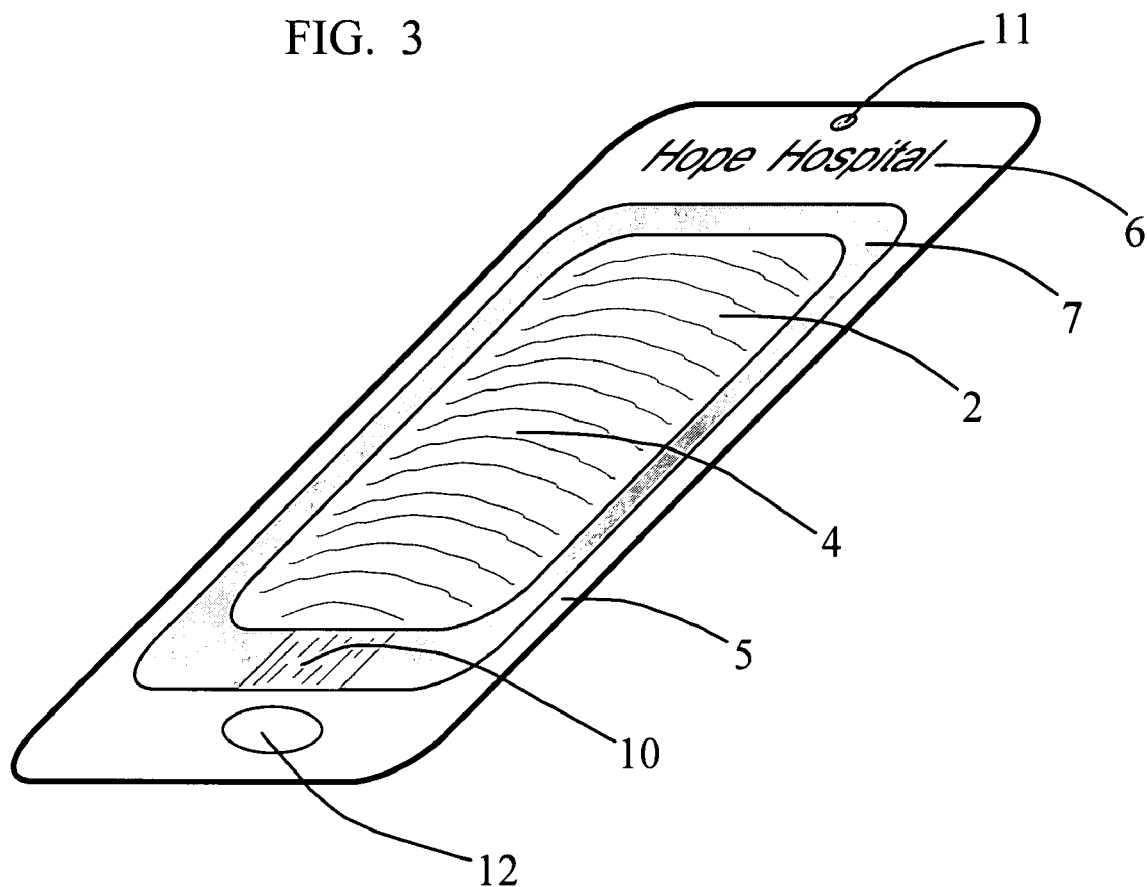
FIG. 3 is a frontal perspective view of a simple embodiment of a disposable dispenser package with a single blister well 2 formed in a flexible top film containing a multiple application of hand sanitizing fluid 4, sealed to a stiff backing 5 in accordance with the principle of the present invention.
Figure 4:
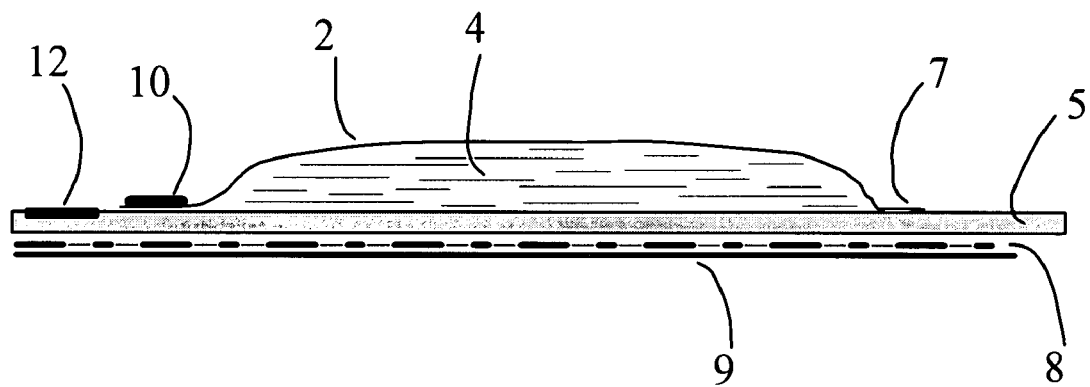
FIG. 4 is across-sectional side view showing the relationship of the single well 2, backing 5, sealing areas 7, affixing adhesive 8, and a removable cover 9 on the adhesive.

The dispenser is in the form of a common blister package card that contains only one well containing hand sanitizing fluid. Graphic representation of an embodiment of a single well, multiple dose, disposable dispenser package is shown in FIG. 3 and FIG. 4. A single well 2 formed of flexible polymeric film (2-mil clear, coextruded polypropylene/polyvinyldichloride/polypropylene) encloses and contains multiple doses of hand sanitizing fluid 4 (62% ethanol). The film with its filled well 2 has a peripheral seal 7 with a relatively stiff non-rupturable backing 5 that facilitate handling by hands of varying size and strength, necessitates blister well side dispersement and effectively lids each of the wells 2. Creation of the seal can be achieved by a number of means well known in the art, herein the common technique involving heat and pressure is used to create the seal 7. Also illustrated is a release point 10 for the fluid 4 in the form of a self-closing tension valve which opens under fluidic pressure generated by finger pressure on the flexible film forming the well 2 surface. Immediately adjacent to the release point 10 so as to be wetted by the fluid 4 released is a timing dot 12 that can indicate the elapsed time since the fluid dispersal. Further illustrated in FIG. 3 is a mark 6 functioning as a simple cuing means for the package. A hole 11 for a lanyard or clip fastener in the package provides an example of one of many possible attachment mechanisms. FIG. 4 shows the elements of FIG. 3 laid out as a cross-section which further depicts another example of a package attachment means herein shown as an adhesive 8 with a removable cover 9. The single well is formed in the manner described in Example 1 with the same features of a flexible upper blister and stiffer lower backing encapsulation a quantity of hand sanitizing fluid. In this case the amount of fluid is typically 5 to 60 milliliters and permits several applications dosages to be released as contrasted with the single-use emptying of the blister dispenser/containers of Example 1. The strapping system, pressure manipulations, blister forms, closure means, and strap attachment descriptions of Example 1 are also the same and are whereby incorporated in this example. However, in that the dispenser is to provide multiple dose applications the predetermined fluid release openings need to be closed following a discharge of fluid to preserve the remaining material. This valve requirement can be met by any of a vast number of types known to the art and all are envisioned under the general engineering subject of valves. Two in way of example and by their simplicity that could be of particular value on a disposable dispenser package are herein described. The first, is a simple one-way flap valve that, working in conjunction with the well-know clogging properties of viscous liquids and gels like the hand sanitizing fluids currently marketed, forms an adequate sealing means after each dosage release. The second is a simple self-closing slit or puncture opening that again partially relies on the clogging and evaporative properties of the hand sanitizing fluid to seal the opening. While this description of a single reservoir dispenser has been that of a flat blister, a dispenser container of a conventional shape as might be described as a vial or bottle with conventional caps are also envisioned. Configuration shape of the single reservoir dispenser is not critical to measuring compliance monitoring given that the fluid contained in the dispenser can be measured by volume or weight.

The use of a single fluid reservoir eliminates the physical record created by discrete used wells of the plural blister well construct. But a physical record of applications does exist in the volume and mass signatures of the missing or remaining fluids associated with the single reservoir. Given the known and thus predetermined amount of fluid in the dispensers reservoir at the start of the monitoring period, and further given knowing the average amount used in a given dispersed application, it is quite possible to deduce the number of applications deployed in a hand sanitizing acts. This measurement can be made casually by visual or tactile techniques, or by more precise mechanical measurements of volume or weight of the remaining or missing fluids. Either approach gives the same basis for a measuring means of a physical record that, when associated with the time worn, gives a value that gauges the degree of hand compliance of the wearer.

Throughout this application various publications and public documents are referenced. The disclosures of these publications in their entireties are hereby incorporated by reference into this application in order to more fully describe the state of the art to which the invention pertains.

While preferred embodiments of the invention have been discussed and described, modifications and variations may be made thereto by those of ordinary skill in the art without departing from the spirit and scope of the present invention, which is more particularly set forth in the appended claims. In addition, it should be understood that aspects of the various embodiments may be interchanged both in whole or in part. Further, those of ordinary skill in the art will appreciate that the foregoing description is by way of example only, and is not intended to be limitative of the invention so further described in such claims.

What is claimed is:

1. A method for monitoring hand hygiene compliance, comprising:
   providing a plurality of disposable dispensers, each said dispenser comprised of multiple distinct individual units, each said unit containing a known dose of hand sanitizing fluid and capable of dispensing said unit dose on demand;
   distributing at least one of said dispensers to a user to be employed for dispensing said hand sanitizing fluid for individual acts of hand sanitation, each said hand sanitizing fluid dispersement act creating a discrete physical record permanently associated with each said dispenser; and,
   counting said physical records recorded by said dispenser and associating said count with said user when said user submits said dispenser for said counting to derive a number indicating the degree of hand hygiene compliance for said user; and including the step of timing means disposed on each of said disposable dispensers for measuring a duration of time since the dispensing of said fluid for said act of hand sanitizing.

2. The method of claim 1 wherein said dispenser is worn on the wrist of said user.

3. The method of claim 1 wherein said dispenser is worn on the body of said user.

4. The method of claim 1 wherein said dispenser is attached to the body of said user by a lanyard.

5. The method of claim 1 wherein said dispenser is attached to the clothing of said user.

6. The method of claim 1 wherein said dispenser is carried in a pocket of said user.

7. The method of claim 1 wherein said individual units are flexible blister wells each filled with an amount of said hand sanitizing fluid sufficient for a single act of hand sanitizing.

8. The method of claim 7 wherein a discrete said blister well is ruptured in dispensing said fluid whereby the resulting broken form of said ruptured well creates said physical record.

9. The method of claim 7 wherein a discrete said blister well is emptied in dispensing said fluid whereby the emptied said blister well undergoes a shape change thereby creating said physical record.

10. The method of claim 1 wherein said timing means are timing dots wetted by said dispersement of said fluid.

11. The method of claim 1 wherein said timing means are wetted timing dots within said individual units and upon fluid dispersement begin to dry so that at the end of a predetermined period of time reveals or obscures a mark or color.

12. The method of claim 10 or claim 11 whereby the time period for said residual hand sanitizing fluid to substantially evaporate is between 1 minute and 60 minutes.

13. The method of claim 1 wherein said timing means is a predetermined timed chemical process resulting in a recognizable color or mark modification upon completion.

14. The method of claim 1 wherein said counting is a visually count of said physical records to obtain said number.

15. The method of claim 1 wherein said counting is a machine count of said physical records to obtain said number.

16. A method for compliance monitoring of hand hygiene, comprising:
   providing a plurality of disposable dispensers, each said dispenser including a single reservoir of hand sanitizing fluid, said reservoir consisting of multiple individual unit doses of a known quantity of said fluid, and said dispenser capable of dispensing a said unit dose on demand for an act of hand sanitation;
   supplying at least one of said dispensers to a user to be employed for dispensing said hand sanitizing fluid for individual acts of hand sanitation, each said hand sanitizing fluid dispersement act creating a discrete physical record permanently associated with each said dispenser; and,
   counting said physical records recorded by said dispenser and associating said count with said user when said user submits said dispenser for said counting to derive a number indicating the degree of hand hygiene compliance for said user; and including the step of timing means disposed on each of said disposable dispensers for measuring a duration of time since the dispensing of said fluid for said act of hand sanitizing.

17. The method of claim 16 further including a timing means in the form of a timing dot capable of indicating a duration of time since the last dispersement of said fluid for said act of hand sanitizing.

18. The method of claim 16 the body of said user.

19. The method of claim 16 wherein the dispenser is attached to the body of said user by a lanyard.

20. The method of claim 16 wherein the dispenser is attached to clothing of said user.

21. The method of claim 16 wherein the dispenser is carried in a pocket of said user.

22. The method of claim 16 wherein the said counting is to visually or tactilely determine the quantity of remaining or missing said fluid.

23. The method of claim 16 wherein the said counting is to mechanically measure the volume of remaining or missing said fluid in said reservoir.

24. The method of claim 16 wherein the said counting is to mechanically measure the weight of the remaining or missing said in said reservoir.

25. A system for compliance monitoring of hand hygiene, comprising:
   a) a hand sanitizing fluid dispenser worn or carried by a person; and
   b) employing said dispenser equipped with a timing means in the form of a timing dot utilizing mechanical and/or chemical properties to provide visual information regarding elapsed time from last dispersement of said fluid from said dispenser for an act of hand sanitization.

* * * * *